(12) United States Patent
Conlon et al.

(10) Patent No.: US 10,555,750 B2
(45) Date of Patent: Feb. 11, 2020

(54) ULTRASONIC SURGICAL INSTRUMENT WITH REPLACEABLE BLADE HAVING IDENTIFICATION FEATURE

(71) Applicant: Ethicon Endo-Surgery, LLC, Guaynabo, PR (US)

(72) Inventors: Sean P. Conlon, Loveland, OH (US); Jeffrey A. Bullock, Cincinnati, OH (US); Eric Roberson, Cincinnati, OH (US); Jeffrey L. Aldridge, Lebanon, OH (US)

(73) Assignee: Ethicon LLC, Guaynabo, PR (US)

( * ) Notice: Subject to any disclaimer, the term of this patent is extended or adjusted under 35 U.S.C. 154(b) by 298 days.

(21) Appl. No.: 15/246,618

(22) Filed: Aug. 25, 2016

(65) Prior Publication Data
US 2018/0055533 A1    Mar. 1, 2018

(51) Int. Cl.
*A61B 17/32* (2006.01)
*A61B 18/14* (2006.01)
(Continued)

(52) U.S. Cl.
CPC ........... *A61B 17/320092* (2013.01); *A61B 17/320068* (2013.01); *A61B 18/1442* (2013.01);
(Continued)

(58) Field of Classification Search
CPC .... A61B 2090/0814; A61B 17/320092; A61B 18/1442; A61B 2018/1455; A61B 2018/00601; A61B 2090/0803; A61B 2017/320088; A61B 2018/00589; A61B 2018/00595; A61B 1/00062; A61B 2560/028; A61B 1/00103; A61B 5/15142; A61B 2560/0285; A61B 2017/0023;
(Continued)

(56) References Cited

U.S. PATENT DOCUMENTS 5,322,055 A    6/1994    Davison et al.
5,324,299 A    6/1994    Davison et al.
(Continued)

FOREIGN PATENT DOCUMENTS

EP    2 522 285 A1    11/2012
WO    WO 2014/012032 A2    1/2014

OTHER PUBLICATIONS

U.S. Appl. No. 61/410,603, filed Nov. 5, 2010.
(Continued)

*Primary Examiner* — Katrina M Stransky
*Assistant Examiner* — Brigid K Byrd
(74) *Attorney, Agent, or Firm* — Frost Brown Todd LLC

(57) ABSTRACT

An apparatus includes a body, a shaft assembly, an end effector portion, a data storage component, a reader, and a use control. The shaft assembly extends distally from the body and includes a support portion. The end effector portion is configured to selectively couple with the support portion of the shaft assembly. The data storage component is associated with the end effector portion and contains data uniquely associated with the end effector portion. The reader is adapted to read the data from the data storage component. The use control is adapted to enable operation of the end effector portion if the data meets at least one usage parameter.

15 Claims, 11 Drawing Sheets

(51) Int. Cl.
*A61B 90/00* (2016.01)
*A61B 18/00* (2006.01)

(52) U.S. Cl.
CPC .. *A61B 90/39* (2016.02); *A61B 2017/320074* (2017.08); *A61B 2017/320088* (2013.01); *A61B 2017/320094* (2017.08); *A61B 2017/320095* (2017.08); *A61B 2018/0063* (2013.01); *A61B 2018/00589* (2013.01); *A61B 2018/00595* (2013.01); *A61B 2018/00601* (2013.01); *A61B 2018/00994* (2013.01); *A61B 2018/1455* (2013.01); *A61B 2090/0803* (2016.02); *A61B 2090/3937* (2016.02)

(58) Field of Classification Search
CPC ................................. A61B 18/04; A61B 17/320068–2017/320098; A61M 2205/27; A61F 2002/30716; A61F 2250/009; A61F 13/505
USPC .......................................................... 606/27
See application file for complete search history.

(56) References Cited

U.S. PATENT DOCUMENTS

| | | | |
|---|---|---|---|
| 5,400,267 A * | 3/1995 | Denen | A61B 17/00 128/908 |
| 5,873,873 A | 2/1999 | Smith et al. | |
| 5,980,510 A | 11/1999 | Tsonton et al. | |
| 6,283,981 B1 | 9/2001 | Beaupre | |
| 6,308,089 B1 * | 10/2001 | von der Ruhr | A61B 5/00 600/338 |
| 6,309,400 B2 | 10/2001 | Beaupre | |
| 6,325,811 B1 | 12/2001 | Messerly | |
| 6,423,082 B1 | 7/2002 | Houser et al. | |
| 6,773,444 B2 | 8/2004 | Messerly | |
| 6,783,524 B2 | 8/2004 | Anderson et al. | |
| 7,336,533 B2 | 2/2008 | Hunter et al. | |
| 7,568,619 B2 * | 8/2009 | Todd | A61B 90/98 235/385 |
| 7,837,694 B2 * | 11/2010 | Tethrake | A61B 90/00 340/572.1 |
| 8,057,498 B2 | 11/2011 | Robertson | |
| 8,461,744 B2 | 6/2013 | Wiener et al. | |
| 8,591,536 B2 | 11/2013 | Robertson | |
| 8,623,027 B2 | 1/2014 | Price et al. | |
| 8,911,460 B2 | 12/2014 | Neurohr et al. | |
| 8,986,302 B2 | 3/2015 | Aldridge et al. | |
| 9,023,071 B2 | 5/2015 | Miller et al. | |
| 9,095,367 B2 * | 8/2015 | Olson | A61B 34/37 |
| 9,204,920 B2 | 12/2015 | McPherson et al. | |
| 9,241,731 B2 * | 1/2016 | Boudreaux | A61B 17/320068 |
| 9,364,278 B2 * | 6/2016 | DeCarlo | A61B 18/14 |
| 9,381,058 B2 | 7/2016 | Houser et al. | |
| 9,393,037 B2 | 7/2016 | Olson et al. | |
| 9,572,592 B2 | 2/2017 | Price et al. | |
| 9,820,738 B2 * | 11/2017 | Lytle, IV | A61B 90/98 |
| 9,913,642 B2 * | 3/2018 | Leimbach | A61B 17/072 |
| 2004/0186376 A1 * | 9/2004 | Hogg | A61B 1/00059 600/424 |
| 2006/0079874 A1 | 4/2006 | Faller et al. | |
| 2007/0038044 A1 * | 2/2007 | Dobbles | A61B 5/0031 600/316 |
| 2007/0119055 A1 * | 5/2007 | Walen | A61B 17/142 30/144 |
| 2007/0158385 A1 * | 7/2007 | Hueil | A61B 17/07207 227/175.1 |
| 2007/0191713 A1 | 8/2007 | Eichmann et al. | |
| 2007/0282333 A1 | 12/2007 | Fortson et al. | |
| 2008/0164296 A1 * | 7/2008 | Shelton | A61B 17/07207 227/175.1 |
| 2008/0200940 A1 | 8/2008 | Eichmann et al. | |
| 2008/0211634 A1 * | 9/2008 | Hopkins | A61B 1/00016 340/10.1 |
| 2011/0238063 A1 * | 9/2011 | Gregg | A61B 18/1233 606/41 |
| 2011/0270179 A1 * | 11/2011 | Ouyang | A61B 1/00062 604/110 |
| 2011/0295269 A1 * | 12/2011 | Swensgard | A61B 17/068 606/130 |
| 2012/0116265 A1 | 5/2012 | Houser et al. | |
| 2013/0018400 A1 * | 1/2013 | Milton | A61B 17/32002 606/167 |
| 2013/0060109 A1 * | 3/2013 | Besko | A61B 5/6832 600/323 |
| 2013/0096390 A1 * | 4/2013 | Weller-Brophy | A61B 1/00103 600/300 |
| 2013/0253480 A1 * | 9/2013 | Kimball | G06F 19/3481 606/1 |
| 2014/0031726 A1 * | 1/2014 | Chernomorsky | A61B 17/24 601/2 |
| 2014/0246471 A1 * | 9/2014 | Jaworek | A61B 17/068 227/175.1 |
| 2014/0259591 A1 * | 9/2014 | Shelton, IV | A61B 34/30 29/402.03 |
| 2015/0053744 A1 * | 2/2015 | Swayze | A61B 17/072 227/176.1 |
| 2015/0080924 A1 | 3/2015 | Stulen et al. | |
| 2015/0126988 A1 * | 5/2015 | Hinton | A61B 18/02 606/26 |
| 2015/0272575 A1 * | 10/2015 | Leimbach | A61B 17/072 227/175.3 |
| 2015/0272608 A1 * | 10/2015 | Gladstone | A61B 17/320068 606/167 |
| 2016/0089533 A1 * | 3/2016 | Turner | A61B 17/320068 606/34 |
| 2016/0206343 A1 * | 7/2016 | Ross | A61B 17/00234 |
| 2017/0296259 A1 * | 10/2017 | Decarlo | A61B 18/14 |

OTHER PUBLICATIONS

International Search Report dated Nov. 13, 2017 for Application No. PCT/US2017/048337, 6 pgs.
International Preliminary Report on Patentability and Written Opinion dated Feb. 26, 2019 for Application No. PCT/US2017/048337, 8 pgs.

\* cited by examiner

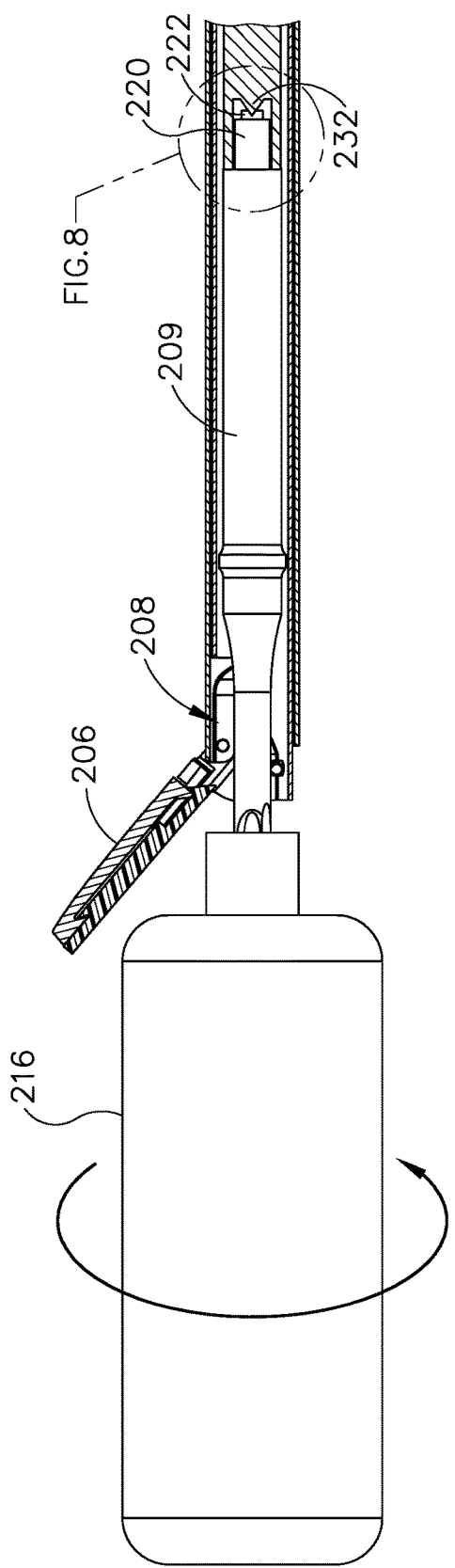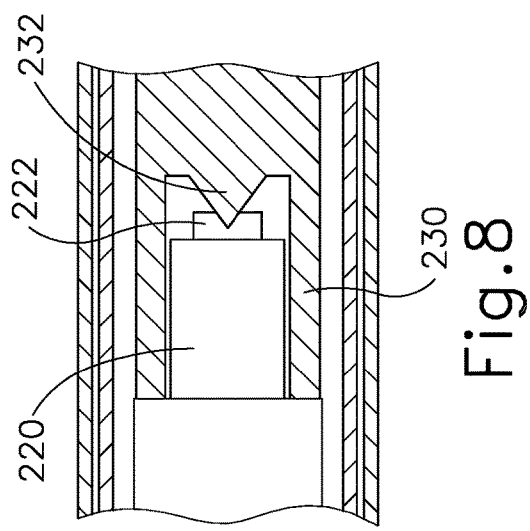

ULTRASONIC SURGICAL INSTRUMENT WITH REPLACEABLE BLADE HAVING IDENTIFICATION FEATURE

BACKGROUND

A variety of surgical instruments include an end effector having a blade element that vibrates at ultrasonic frequencies to cut and/or seal tissue (e.g., by denaturing proteins in tissue cells). These instruments include one or more piezoelectric elements that convert electrical power into ultrasonic vibrations, which are communicated along an acoustic waveguide to the blade element. The precision of cutting and coagulation may be controlled by the operator's technique and adjusting the power level, blade edge angle, tissue traction, and blade pressure.

Examples of ultrasonic surgical instruments include the HARMONIC ACE® Ultrasonic Shears, the HARMONIC WAVE® Ultrasonic Shears, the HARMONIC FOCUS® Ultrasonic Shears, and the HARMONIC SYNERGY® Ultrasonic Blades, all by Ethicon Endo-Surgery, Inc. of Cincinnati, Ohio. Further examples of such devices and related concepts are disclosed in U.S. Pat. No. 5,322,055, entitled "Clamp Coagulator/Cutting System for Ultrasonic Surgical Instruments," issued Jun. 21, 1994, the disclosure of which is incorporated by reference herein; U.S. Pat. No. 5,873,873, entitled "Ultrasonic Clamp Coagulator Apparatus Having Improved Clamp Mechanism," issued Feb. 23, 1999, the disclosure of which is incorporated by reference herein; U.S. Pat. No. 5,980,510, entitled "Ultrasonic Clamp Coagulator Apparatus Having Improved Clamp Arm Pivot Mount," issued Nov. 9, 1999, the disclosure of which is incorporated by reference herein; U.S. Pat. No. 6,283,981, entitled "Method of Balancing Asymmetric Ultrasonic Surgical Blades," issued Sep. 4, 2001, the disclosure of which is incorporated by reference herein; U.S. Pat. No. 6,309,400, entitled "Curved Ultrasonic Blade having a Trapezoidal Cross Section," issued Oct. 30, 2001, the disclosure of which is incorporated by reference herein; U.S. Pat. No. 6,325,811, entitled "Blades with Functional Balance Asymmetries for use with Ultrasonic Surgical Instruments," issued Dec. 4, 2001, the disclosure of which is incorporated by reference herein; U.S. Pat. No. 6,423,082, entitled "Ultrasonic Surgical Blade with Improved Cutting and Coagulation Features," issued Jul. 23, 2002, the disclosure of which is incorporated by reference herein; U.S. Pat. No. 6,773,444, entitled "Blades with Functional Balance Asymmetries for Use with Ultrasonic Surgical Instruments," issued Aug. 10, 2004, the disclosure of which is incorporated by reference herein; U.S. Pat. No. 6,783,524, entitled "Robotic Surgical Tool with Ultrasound Cauterizing and Cutting Instrument," issued Aug. 31, 2004, the disclosure of which is incorporated by reference herein; U.S. Pat. No. 8,057,498, entitled "Ultrasonic Surgical Instrument Blades," issued Nov. 15, 2011, the disclosure of which is incorporated by reference herein; U.S. Pat. No. 8,461,744, entitled "Rotating Transducer Mount for Ultrasonic Surgical Instruments," issued Jun. 11, 2013, the disclosure of which is incorporated by reference herein; U.S. Pat. No. 8,591,536, entitled "Ultrasonic Surgical Instrument Blades," issued Nov. 26, 2013, the disclosure of which is incorporated by reference herein; and U.S. Pat. No. 8,623,027, entitled "Ergonomic Surgical Instruments," issued Jan. 7, 2014, the disclosure of which is incorporated by reference herein.

Still further examples of ultrasonic surgical instruments are disclosed in U.S. Pub. No. 2006/0079874, entitled "Tissue Pad for Use with an Ultrasonic Surgical Instrument," published Apr. 13, 2006, now abandoned, the disclosure of which is incorporated by reference herein; U.S. Pub. No. 2007/0191713, entitled "Ultrasonic Device for Cutting and Coagulating," published Aug. 16, 2007, now abandoned, the disclosure of which is incorporated by reference herein; U.S. Pub. No. 2007/0282333, entitled "Ultrasonic Waveguide and Blade," published Dec. 6, 2007, now abandoned, the disclosure of which is incorporated by reference herein; U.S. Pub. No. 2008/0200940, entitled "Ultrasonic Device for Cutting and Coagulating," published Aug. 21, 2008, now abandoned, the disclosure of which is incorporated by reference herein; U.S. Pub. No. 2008/0234710, entitled "Ultrasonic Surgical Instruments," published Sep. 25, 2008, issued as U.S. Pat. No. 8,911,460 on Dec. 16, 2014, the disclosure of which is incorporated by reference herein; and U.S. Pub. No. 2010/0069940, entitled "Ultrasonic Device for Fingertip Control," published Mar. 18, 2010, issued as U.S. Pat. No. 9,023,071 on May 5, 2015, the disclosure of which is incorporated by reference herein.

Some ultrasonic surgical instruments may include a cordless transducer such as that disclosed in U.S. Pub. No. 2012/0112687, entitled "Recharge System for Medical Devices," published May 10, 2012, issued as U.S. Pat. No. 9,381,058 on Jul. 5, 2016, the disclosure of which is incorporated by reference herein; U.S. Pub. No. 2012/0116265, entitled "Surgical Instrument with Charging Devices," published May 10, 2012, now abandoned, the disclosure of which is incorporated by reference herein; and/or U.S. Pat. App. No. 61/410,603, filed Nov. 5, 2010, entitled "Energy-Based Surgical Instruments," the disclosure of which is incorporated by reference herein.

Additionally, some ultrasonic surgical instruments may include an articulating shaft section. Examples of such ultrasonic surgical instruments are disclosed in U.S. Pub. No. 2014/0005701, published Jan. 2, 2014, issued as U.S. Pat. No 9,393,037 on Jul. 19, 2016, entitled "Surgical Instruments with Articulating Shafts," the disclosure of which is incorporated by reference herein; and U.S. Pub. No. 2014/0114334, published Apr. 24, 2014, issued as U.S. Pat. No 9,095,367 on Aug. 4, 2015, entitled "Flexible Harmonic Waveguides/Blades for Surgical Instruments," the disclosure of which is incorporated by reference herein.

While several surgical instruments and systems have been made and used, it is believed that no one prior to the inventors has made or used the invention described in the appended claims.

BRIEF DESCRIPTION OF THE DRAWINGS

While the specification concludes with claims which particularly point out and distinctly claim this technology, it is believed this technology will be better understood from the following description of certain examples taken in conjunction with the accompanying drawings, in which like reference numerals identify the same elements and in which:

FIG. 7B depicts a side elevational view of the distal end of the shaft assembly of the instrument of FIG. 3, with the shaft assembly shown in cross-section, showing the distal portion of the waveguide and blade having been assembled therewith via the blade cartridge;

FIG. 8 depicts a detailed view of a spike in the distal end of the proximal portion of the waveguide of the shaft assembly of the instrument of FIG. 3 fracturing a feature at the proximal end of the distal portion of the waveguide;

Figure 1:
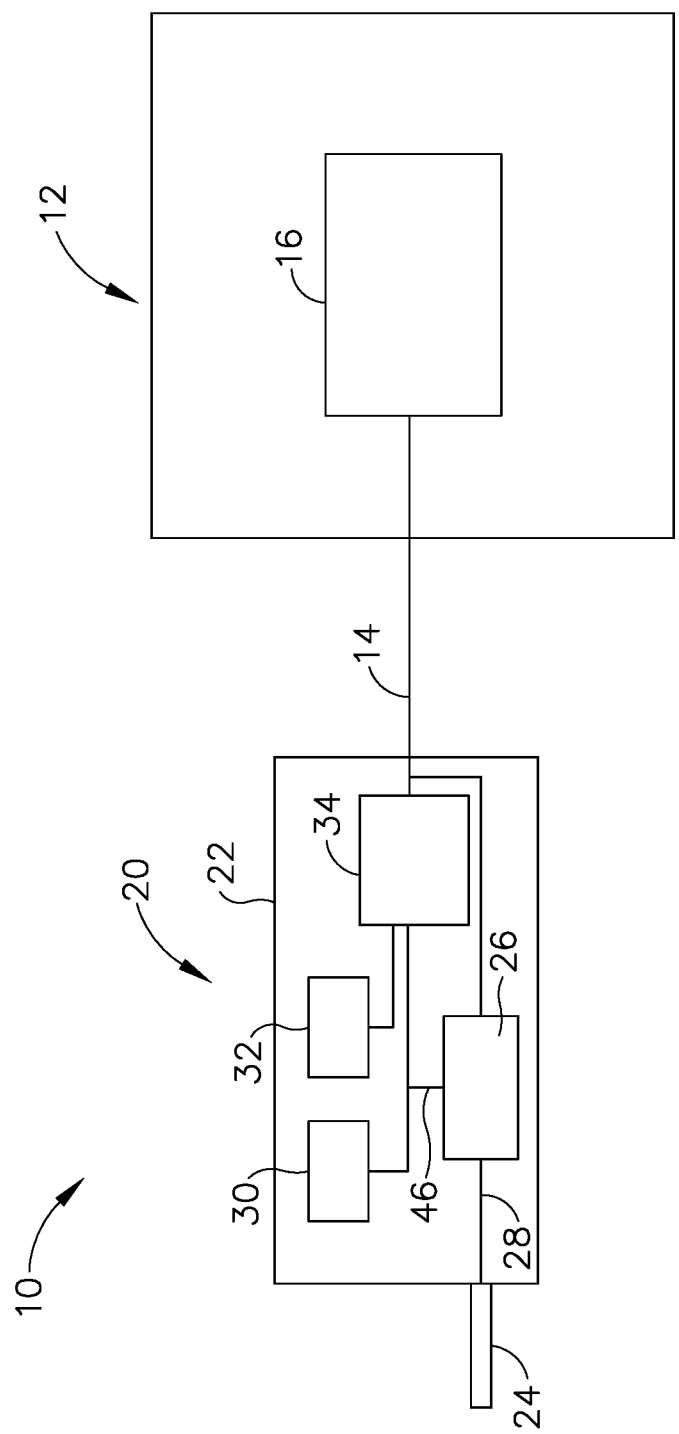
FIG. 1 depicts a block schematic view of an exemplary surgical system.

The drawings are not intended to be limiting in any way, and it is contemplated that various embodiments of the technology may be carried out in a variety of other ways, including those not necessarily depicted in the drawings. The accompanying drawings incorporated in and forming a part of the specification illustrate several aspects of the present technology, and together with the description serve to explain the principles of the technology; it being understood, however, that this technology is not limited to the precise arrangements shown.

DETAILED DESCRIPTION

The following description of certain examples of the technology should not be used to limit its scope. Other examples, features, aspects, embodiments, and advantages of the technology will become apparent to those skilled in the art from the following description, which is by way of illustration, one of the best modes contemplated for carrying out the technology. As will be realized, the technology described herein is capable of other different and obvious aspects, all without departing from the technology. Accordingly, the drawings and descriptions should be regarded as illustrative in nature and not restrictive.

It is further understood that any one or more of the teachings, expressions, embodiments, examples, etc. described herein may be combined with any one or more of the other teachings, expressions, embodiments, examples, etc. that are described herein. The following-described teachings, expressions, embodiments, examples, etc. should therefore not be viewed in isolation relative to each other. Various suitable ways in which the teachings herein may be combined will be readily apparent to those of ordinary skill in the art in view of the teachings herein. Such modifications and variations are intended to be included within the scope of the claims.

For clarity of disclosure, the terms "proximal" and "distal" are defined herein relative to an operator or other operator grasping a surgical instrument having a distal surgical end effector. The term "proximal" refers to the position of an element closer to the operator or other operator and the term "distal" refers to the position of an element closer to the surgical end effector of the surgical instrument and further away from the operator or other operator.

I. Overview of Exemplary Ultrasonic Surgical System

FIG. 1 shows components of an exemplary surgical system (10) in diagrammatic block form. As shown, system (10) comprises an ultrasonic generator (12) and an ultrasonic surgical instrument (20). As will be described in greater detail below, instrument (20) is operable to cut tissue and seal or weld tissue (e.g., a blood vessel, etc.) substantially simultaneously, using ultrasonic vibrational energy. Generator (12) and instrument (20) are coupled together via cable (14). Cable (14) may comprise a plurality of wires; and may provide unidirectional electrical communication from generator (12) to instrument (20) and/or bidirectional electrical communication between generator (12) and instrument (20). Some versions of system (10) may incorporate generator (12) into instrument (20), such that cable (14) may simply be omitted.

By way of example only, generator (12) may comprise the GEN04 or GEN11 sold by Ethicon Endo-Surgery, Inc. of Cincinnati, Ohio. In addition, or in the alternative, generator (12) may be constructed in accordance with at least some of the teachings of U.S. Pub. No. 2011/0087212, entitled "Surgical Generator for Ultrasonic and Electrosurgical Devices," published Apr. 14, 2011, issued as U.S. Pat. No. 8,986,302 on Mar. 24, 2015, the disclosure of which is incorporated by reference herein. Alternatively, any other suitable generator (12) may be used. As will be described in greater detail below, generator (12) is operable to provide power to instrument (20) to perform ultrasonic surgical procedures.

Instrument (20) comprises a handle assembly (22), which is configured to be grasped in one hand (or two hands) of an operator and manipulated by one hand (or two hands) of the operator during a surgical procedure. For instance, in some versions, handle assembly (22) may be grasped like a pencil by the operator. In some other versions, handle assembly (22) may include a scissor grip that may be grasped like scissors by the operator. In some other versions, handle assembly (22) may include a pistol grip that may be grasped like a pistol by the operator. Of course, handle assembly (22) may be configured to be gripped in any other suitable fashion. Furthermore, some versions of instrument (20) may substitute handle assembly (22) with a body that is coupled to a robotic surgical system that is configured to operate instrument (e.g., via remote control, etc.). In the present example, a blade (24) extends distally from the handle assembly (22). Handle assembly (22) includes an ultrasonic transducer (26) and an ultrasonic waveguide (28), which couples ultrasonic transducer (26) with blade (24). Ultrasonic transducer (26) receives electrical power from generator (12) via cable (14). By virtue of its piezoelectric properties, ultrasonic transducer (26) is operable to convert such electrical power into ultrasonic vibrational energy.

Ultrasonic waveguide (28) may be flexible, semi-flexible, rigid, or have any other suitable properties. As noted above, ultrasonic transducer (26) is integrally coupled with blade (24) via ultrasonic waveguide (28). In particular, when ultrasonic transducer (26) is activated to vibrate at ultrasonic frequencies, such vibrations are communicated through ultrasonic waveguide (28) to blade (24), such that blade (24) will also vibrate at ultrasonic frequencies. When blade (24) is in an activated state (i.e., vibrating ultrasonically), blade (24) is operable to effectively cut through tissue and seal tissue. Ultrasonic transducer (26), ultrasonic waveguide (28), and blade (24) together thus form an acoustic assembly providing ultrasonic energy for surgical procedures when powered by generator (12). Handle assembly (22) is configured to substantially isolate the operator from the vibrations of the acoustic assembly formed by transducer (26), ultrasonic waveguide (28), and blade (24).

In some versions, ultrasonic waveguide (28) may amplify the mechanical vibrations transmitted through ultrasonic waveguide (28) to blade (24). Ultrasonic waveguide (28) may further have features to control the gain of the longitudinal vibration along ultrasonic waveguide (28) and/or features to tune ultrasonic waveguide (28) to the resonant frequency of system (10). For instance, ultrasonic waveguide (28) may have any suitable cross-sectional dimensions/configurations, such as a substantially uniform cross-section, be tapered at various sections, be tapered along its entire length, or have any other suitable configuration. Ultrasonic waveguide (28) may, for example, have a length substantially equal to an integral number of one-half system wavelengths ($n\lambda/2$). Ultrasonic waveguide (28) and blade (24) may be fabricated from a solid core shaft constructed out of a material or combination of materials that propagates ultrasonic energy efficiently, such as titanium alloy (e.g., Ti-6Al-4V), aluminum alloys, sapphire, stainless steel, or any other acoustically compatible material or combination of materials.

Those of ordinary skill in the art will understand that, as a matter of physics, the distal end of blade (24) is located at a position corresponding to an anti-node associated with resonant ultrasonic vibrations communicated through waveguide (28) (i.e., at an acoustic anti-node). When transducer (26) is energized, the distal end of blade (24) is configured to move longitudinally in the range of, for example, approximately 10 to 500 microns peak-to-peak, and in some instances in the range of about 20 to about 200 microns at a predetermined vibratory frequency $f_o$ of, for example, 55.5 kHz. When transducer (26) of the present example is activated, these mechanical oscillations are transmitted through waveguide (28) to reach blade (24), thereby providing oscillation of blade (24) at the resonant ultrasonic frequency. Thus, the ultrasonic oscillation of blade (24) may simultaneously sever the tissue and denature the proteins in adjacent tissue cells, thereby providing a coagulative effect with relatively little thermal spread. In some versions, an electrical current may also be provided through blade (24) to also cauterize the tissue.

By way of example only, ultrasonic waveguide (28) and blade (24) may comprise components sold under product codes SNGHK and SNGCB by Ethicon Endo-Surgery, Inc. of Cincinnati, Ohio. By way of further example only, ultrasonic waveguide (28) and/or blade (24) may be constructed and operable in accordance with the teachings of U.S. Pat. No. 6,423,082, entitled "Ultrasonic Surgical Blade with Improved Cutting and Coagulation Features," issued Jul. 23, 2002, the disclosure of which is incorporated by reference herein. As another merely illustrative example, ultrasonic waveguide (28) and/or blade (24) may be constructed and operable in accordance with the teachings of U.S. Pat. No. 5,324,299, entitled "Ultrasonic Scalpel Blade and Methods of Application," issued Jun. 28, 1994, the disclosure of which is incorporated by reference herein. Other suitable properties and configurations of ultrasonic waveguide (28) and blade (24) will be apparent to those of ordinary skill in the art in view of the teachings herein.

Handle assembly (22) of the present example also includes a control selector (30) and an activation switch (32), which are each in communication with a circuit board (34). By way of example only, circuit board (34) may comprise a conventional printed circuit board, a flex circuit, a rigid-flex circuit, or may have any other suitable configuration. Control selector (30) and activation switch (32) may be in communication with circuit board (34) via one or more wires, traces formed in a circuit board or flex circuit, and/or in any other suitable fashion. Circuit board (34) is coupled with cable (14), which is in turn coupled with control circuitry (16) within generator (12). Activation switch (32) is operable to selectively activate power to ultrasonic transducer (26). In particular, when switch (32) is activated, such activation provides communication of appropriate power to ultrasonic transducer (26) via cable (14). By way of example only, activation switch (32) may be constructed in accordance with any of the teachings of the various references cited herein. Other various forms that activation switch (32) may take will be apparent to those of ordinary skill in the art in view of the teachings herein.

In the present example, surgical system (10) is operable to provide at least two different levels or types of ultrasonic energy (e.g., different frequencies and/or amplitudes, etc.) at blade (24). To that end, control selector (30) is operable to permit the operator to select a desired level/amplitude of ultrasonic energy. By way of example only, control selector (30) may be constructed in accordance with any of the teachings of the various references cited herein. Other various forms that control selector (30) may take will be apparent to those of ordinary skill in the art in view of the teachings herein. In some versions, when an operator makes a selection through control selector (30), the operator's selection is communicated back to control circuitry (16) of generator (12) via cable (14), and control circuitry (16) adjusts the power communicated from generator (12) accordingly the next time the operator actuates activation switch (32).

It should be understood that the level/amplitude of ultrasonic energy provided at blade (24) may be a function of characteristics of the electrical power communicated from generator (12) to instrument (20) via cable (14). Thus, control circuitry (16) of generator (12) may provide electrical power (via cable (14)) having characteristics associated with the ultrasonic energy level/amplitude or type selected through control selector (30). Generator (12) may thus be operable to communicate different types or degrees of electrical power to ultrasonic transducer (26), in accordance with selections made by the operator via control selector (30). In particular, and by way of example only, generator (12) may increase the voltage and/or current of the applied signal to increase the longitudinal amplitude of the acoustic assembly. As a merely illustrative example, generator (12) may provide selectability between a "level 1" and a "level 5," which may correspond with a blade (24) vibrational resonance amplitude of approximately 45 microns and approximately 90 microns, respectively. Various ways in which control circuitry (16) may be configured will be apparent to those of ordinary skill in the art in view of the teachings herein. It should also be understood that control selector (30) and activation switch (32) may be substituted with two or more activation switches (32). In some such versions, one activation switch (32) is operable to activate blade (24) at one power level/type while another activation switch (32) is operable to activate blade (24) at another power level/type, etc.

In some alternative versions, control circuitry (16) is located within handle assembly (22). For instance, in some such versions, generator (12) only communicates one type of electrical power (e.g., just one voltage and/or current available) to handle assembly (22), and control circuitry (16) within handle assembly (22) is operable to modify the electrical power (e.g., the voltage of the electrical power), in accordance with selections made by the operator via control selector (30), before the electrical power reaches ultrasonic transducer (26). Furthermore, generator (12) may be incorporated into handle assembly (22) along with all other components of surgical system (10). For instance, one or more batteries (not shown) or other portable sources of power may be provided in handle assembly (22). Still other suitable ways in which the components depicted in FIG. 1 may be rearranged or otherwise configured or modified will be apparent to those of ordinary skill in the art in view of the teachings herein.

II. Overview of Exemplary Ultrasonic Surgical Instrument

The following discussion relates to various exemplary components and configurations for instrument (20). It should be understood that the various examples of instrument (20) described below may be readily incorporated into a surgical system (10) as described above. It should also be understood that the various components and operability of instrument (20) described above may be readily incorporated into the exemplary versions of instrument (110) described below. Various suitable ways in which the above and below teachings may be combined will be apparent to those of ordinary skill in the art in view of the teachings herein. It should also be understood that the below teachings may be readily combined with the various teachings of the references that are cited herein.

Figure 2:
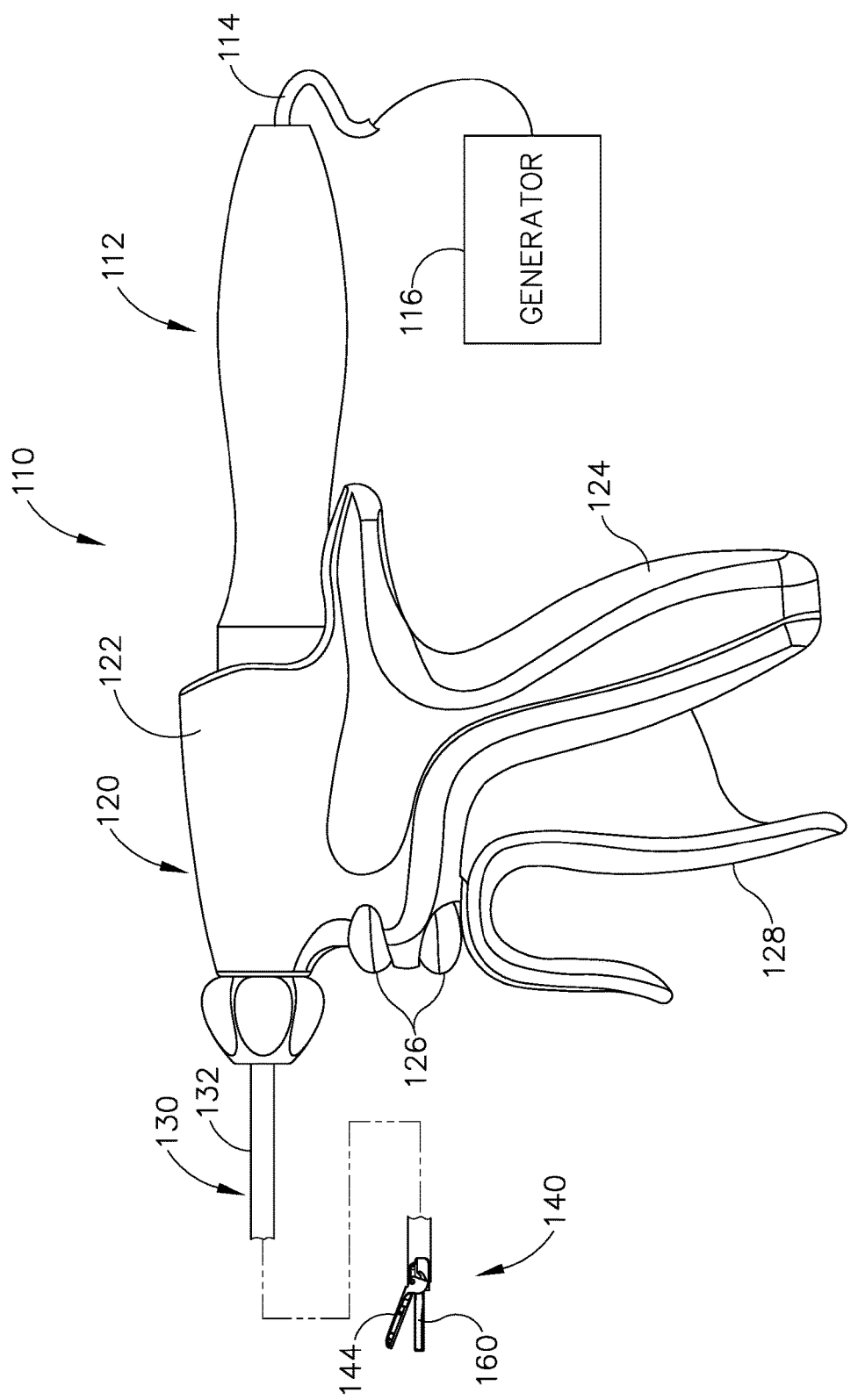
FIG. 2 depicts a side elevational view of an exemplary form that an instrument of the system of FIG. 1 may take.

FIG. 2 illustrates an exemplary ultrasonic surgical instrument (110). At least part of instrument (110) may be constructed and operable in accordance with at least some of the teachings of U.S. Pat. No. 5,322,055; U.S. Pat. No. 5,873, 873; U.S. Pat. No. 5,980,510; U.S. Pat. No. 6,325,811; U.S. Pat. No. 6,773,444; U.S. Pat. No. 6,783,524; U.S. Pat. No. 8,461,744; U.S. Pub. No. 2009/0105750, issued as U.S. Pat. No. 8,623,027 on Jan. 7, 2014; U.S. Pub. No. 2006/0079874, now abandoned; U.S. Pub. No. 2007/0191713, now abandoned; U.S. Pub. No. 2007/0282333, now abandoned; U.S. Pub. No. 2008/0200940, now abandoned; U.S. Pub. No. 2010/0069940 issued as U.S. Pat. No. 9,023,071 on May 5, 2015; U.S. Pub. No. 2012/0112687, issued as U.S. Pat. No. 9,381,058 on Jul. 5, 2016; U.S. Pub. No. 2012/0116265, now abandoned; U.S. Pub. No. 2014/0005701, issued as U.S. Pat. No 9,393,037 on Jul. 19, 2016; U.S. Pat. Pub. No. 2014/0114334, issued as U.S. Pat. No. 9,095,367 on Aug. 4, 2015; U.S. patent application Ser. No. 14/028,717, issued as U.S. Pat. No. 10,172,636 on Jan. 8, 2019; and/or U.S. Pat. App. No. 61/410,603. The disclosures of each of the foregoing patents, publications, and applications are incorporated by reference herein. As described therein and as will be described in greater detail below, instrument (110) is operable to cut tissue and seal or weld tissue substantially simultaneously.

Instrument (110) of the present example comprises a handle assembly (120), a shaft assembly (130), and an end effector (140). Handle assembly (120) comprises a body (122) including a pistol grip (124) and a pair of buttons (126). Handle assembly (120) also includes a trigger (128) that is pivotable toward and away from pistol grip (124). It should be understood, however, that various other suitable configurations may be used, including but not limited to a scissor grip configuration. End effector (140) includes an ultrasonic blade (160) and a pivoting clamp arm (144). Ultrasonic blade (160) may be configured and operable just like ultrasonic blade (24) described above.

Clamp arm (144) is pivotably coupled with an inner tube (not shown in FIG. 2) and an outer tube (132) that form shaft assembly (130). Such an inner and outer tube configuration may be provided in accordance with the teachings of various references that are cited herein. Clamp arm (144) is further coupled with trigger (128). Trigger (128) is operable to drive one of the tubes of shaft assembly (130) longitudinally while the other tube of shaft assembly (130) remains stationary. This relative longitudinal movement between the tubes of shaft assembly (130) provides pivotal movement of clamp arm (144). Clamp arm (144) is thus pivotable toward ultrasonic blade (160) in response to pivoting of trigger (128) toward pistol grip (124); and clamp arm (144) is pivotable away from ultrasonic blade (160) in response to pivoting of trigger (128) away from pistol grip (124). Clamp arm (144) is thereby operable to cooperate with ultrasonic blade (160) to grasp and release tissue; and clamp arm (144) is further operable to compress tissue against ultrasonic blade (160) to thereby enhance the transfer of ultrasonic energy from ultrasonic blade (160) to the tissue. Various suitable ways in which clamp arm (144) may be coupled with trigger (128) will be apparent to those of ordinary skill in the art in view of the teachings herein. In some versions, one or more resilient members are used to bias clamp arm (144) and/or trigger (128) to the open position shown in FIG. 2.

An ultrasonic transducer assembly (112) extends proximally from body (122) of handle assembly (120). Transducer assembly (112) may be configured and operable just like transducer (26) described above. Transducer assembly (112) is coupled with a generator (116) via a cable (114). It should be understood that transducer assembly (112) receives electrical power from generator (116) and converts that power into ultrasonic vibrations through piezoelectric principles. Generator (116) may be configured and operable like generator (12) described above. Generator (116) may thus include a power source and control module that is configured to provide a power profile to transducer assembly (112) that is particularly suited for the generation of ultrasonic vibrations through transducer assembly (112). It should also be understood that at least some of the functionality of generator (116) may be integrated into handle assembly (120), and that handle assembly (120) may even include a battery or other on-board power source such that cable (114) is omitted. Still other suitable forms that generator (116) may take, as well as various features and operabilities that generator (116) may provide, will be apparent to those of ordinary skill in the art in view of the teachings herein.

As shown in FIG. 2, by way of example, one of the buttons (126) may be associated with a "seal" mode, such that actuating the particular one of the buttons (126) only seals tissue, but does not cut tissue, when the tissue is being clamped between clamp arm (144) and blade (160). In particular, activation of a first one of the buttons (126) may cause vibration of ultrasonic blade (160) at a relatively low amplitude. Similarly, by way of further example, the other of the buttons (126) may be associated with a "cut and seal" mode such that actuating the particular one of the buttons (126) may seal and cut tissue when the tissue is being clamped between clamp arm (144) and blade (160). In particular, activation of a second one of the buttons (126) may cause vibration of ultrasonic blade (160) at a relatively high amplitude. Other suitable operational modes that may be associated with buttons (126) will be apparent to persons skilled in the art in view of the teachings herein.

III. Exemplary Alternative Ultrasonic Surgical Instrument

Not all surgical instrument components wear at the same rate. For example, in reference to exemplary surgical instrument (110), ultrasonic blade (160) may wear faster and become unusable sooner than other components of surgical instrument (110). Shaft assembly (130) may have a longer useable life than the components that comprise end effector (140), and transducer assembly (112) may have yet a longer useable life. To ensure that components are not used beyond their usable life, all or a group of the components of a surgical instrument may be designed to be discarded after a single use or a limited number of uses. For example, shaft assembly (130) with end effector (140) may be removable as a unit from body (120) so that the entire unit can be replaced once ultrasonic blade (160) has reached its usable life, even though shaft assembly (130) has remaining usable life.

It should also be understood that ultrasonic blade (160) may provide different operational characteristics based the structural configuration of ultrasonic blade (160). In other words, an ultrasonic blade (160) having one particular structural configuration may provide very different operational characteristics as compared to the operational characteristics provided by an ultrasonic blade (160) having a different structural configuration. It may be desirable to enable an end user to select from various ultrasonic blades (160) having different structural configurations, in order to provide a selected set of operational characteristics that are best suited for the particular task at hand. While providing such modularity and selectability of ultrasonic blades (160), it may be desirable to further ensure that such modular ultrasonic blades (160) are not used beyond their intended working life.

In the present example, it is contemplated that an end effector, such as comprising an ultrasonic blade, having a shorter usable life than other components, be releasably coupleable to a component of the surgical instrument which has a longer usable life. To prevent any use beyond its usable life of such an end effector, which may be not clean, may be beyond its usable life, or may be damaged, the surgical system may determine, based on data associated with the particular end effector, whether that end effector may be used.

A. Exemplary Surgical Instrument with Non-Volatile Electronic Data Storage

Figure 3:
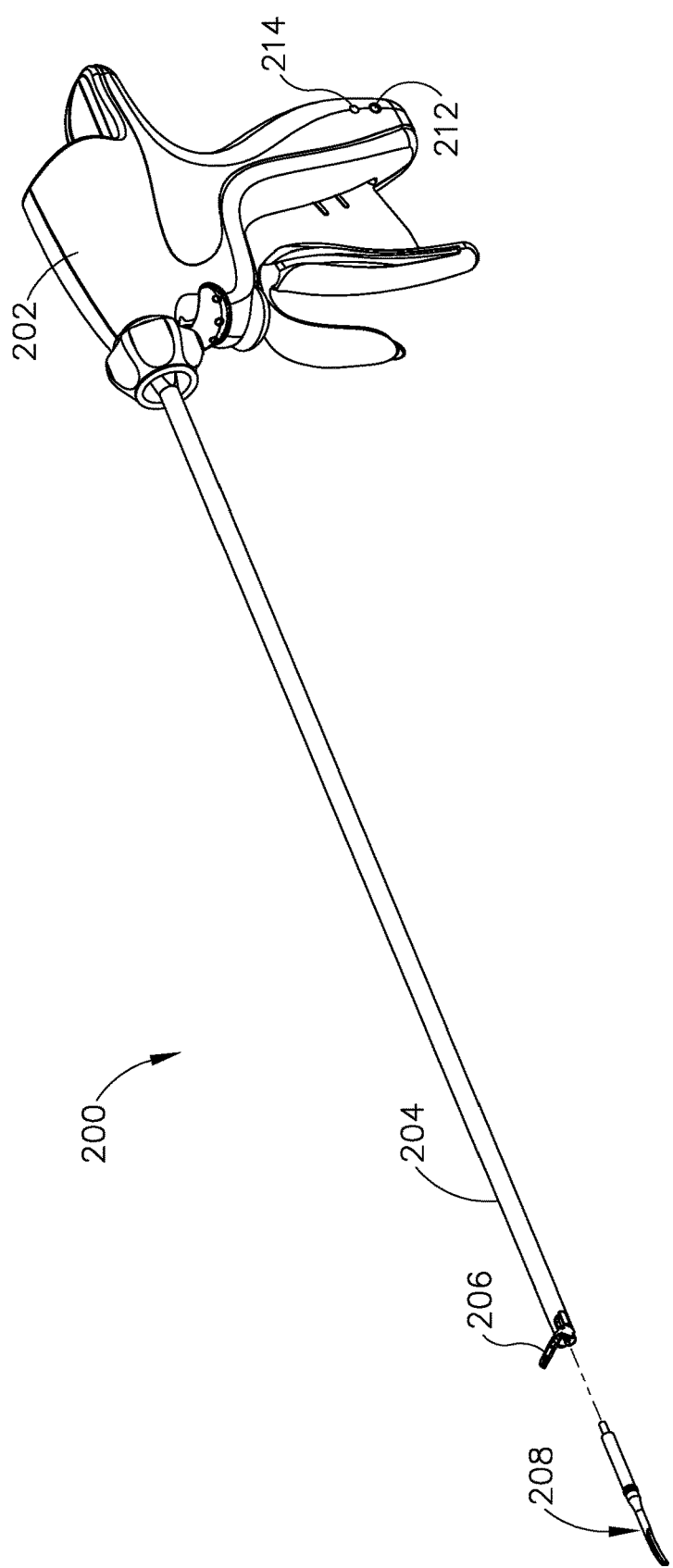
FIG. 3 depicts a top perspective, unassembled view of a portion of an exemplary alternative surgical instrument that may be incorporated into the system of FIG. 1, showing an alternative waveguide assembly including a proximal portion and a distal portion having an ultrasonic blade.

FIG. 3 shows a portion of an alternative exemplary surgical instrument (200) which may be incorporated into the system of FIG. 1. Surgical instrument (200) comprises body (202), shaft assembly (204), clamp arm (206) and distal acoustic portion (208). Clamp arm (206) is pivotably coupled with shaft assembly (204) at the distal end of shaft assembly (204), with shaft assembly (204) adapted to effect the operation of clamp arm (206) (i.e., to pivot clamp arm (206) toward and away from the longitudinal axis of shaft assembly (204)). Distal acoustic portion (208) is releasably coupleable with a proximal portion of waveguide (228) in shaft assembly (204), though distal acoustic portion (208) is shown uncoupled in FIG. 3. Proximal portion of waveguide (228) is operable to communicate ultrasonic vibrations to distal acoustic portion (208) when distal acoustic portion (208) is coupled thereto.

In the present example, distal acoustic portion (208) comprises an ultrasonic blade (207) and a distal waveguide portion (209). In this configuration, distal acoustic portion (208) vibrates at ultrasonic frequencies when operated. It is to be understood that this alternative exemplary surgical instrument is not limited to such an ultrasonic instrument configuration. In other words, the teachings herein may be readily applied to non-ultrasonic surgical instruments, including but not limited to surgical staplers, RF electrosurgical instruments, and various other kinds of instruments. Various suitable ways in which the teachings herein may be applied to various non-ultrasonic surgical instruments will be apparent to those of ordinary skill in the art.

Figure 4:
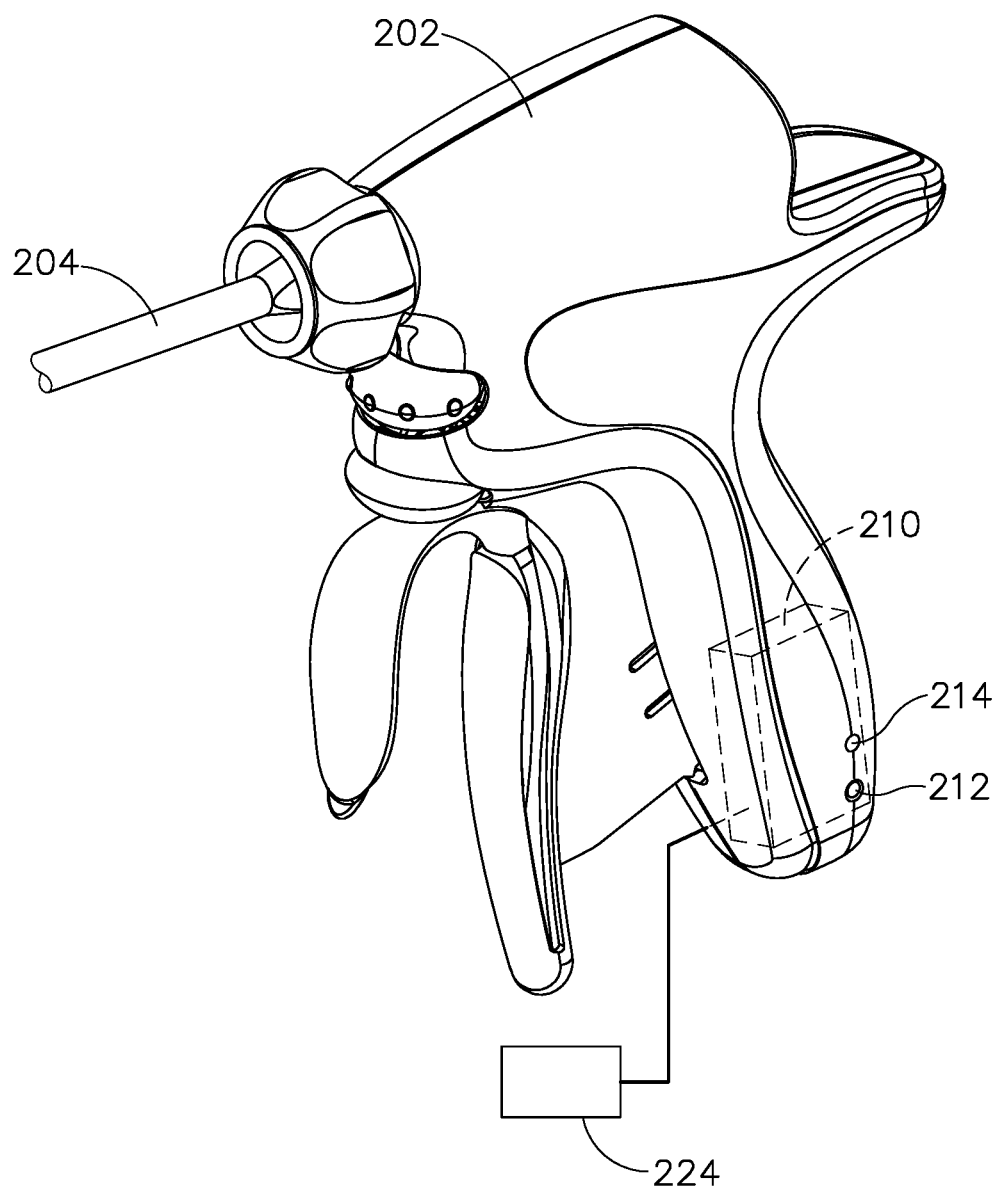
FIG. 4 depicts a perspective view of a handle assembly of the instrument of FIG. 3.

Referring also to FIG. 4, the system may include reader (210) which is adapted to read data related to distal acoustic portion (208) stored in a data storage component (discussed below) associated with distal acoustic portion (208). Reader (210) may be carried by body (202), such as by being disposed there within. Body (202) includes aperture (212) which is adapted to receive the proximal portion of distal acoustic portion (208), where the data storage component may be disposed, and to guide such proximal portion of distal acoustic portion (208) into proximity with reader (210) so that the data related to distal acoustic portion (208) can be read.

Body (202) of the present example also includes indicator (214), such as light, which may provide an indication that the data storage component has been read and an indication whether distal acoustic portion (208) can be used. Reader (210) may be located in any suitable location, including a location separate from body (202). By way of example, indicator (214) may comprise one or more LED lights that are configured to emit a first color (e.g., red) when reader (210) determines that distal acoustic portion (208) cannot be used; and a second color (e.g., green) when reader (210) determines that distal acoustic portion (208) can be used. Indicator (214) may also be operable to provide other forms of visual feedback (e.g., a pattern of flashes, etc.) indicating the type of blade (207) of distal acoustic portion (208) and/or other information. Various suitable forms that indicator (214) may take, and various alternative operabilities that indicator (214) may provide, will be apparent to those of ordinary skill in the art in view of the teachings herein. In some variations, indicator (214) is provided remotely (e.g., via a display on generator (116)). In some other variations, indicator (214) is omitted entirely. It should therefore be understood that indicator (214) is merely optional.

Identifying data and/or use data read by, reader (210) is communicated to use control module (224). While various embodiments may be described in terms of modules and/or blocks to facilitate description, such modules and/or blocks may be implemented by one or more hardware components, e.g., processors, Digital Signal Processors (DSPs), Programmable Logic Devices (PLDs), Application Specific Integrated Circuits (ASICs), circuits, registers and/or software components, e.g., programs subroutines, logic and/or combinations of hardware and software components. While use control module (22) is shown in FIG. 4 as being separate from body (202), it should be understood that use control module (22) may be located within body (202). As another merely illustrative example, use control module (224) may, be incorporated into generator (116). In some such versions, the hardware of a conventional generator (116) may be configured using software and/or firmware to provide the operability of use control module (224) as described below. For example, control circuitry (16) may comprise a generator module comprising a hardware component implemented as a processor for executing program instructions for monitoring various measurable characteristics of the devices, including the identifying and/or use data, and generating a corresponding output drive signal or signals for operating the surgical instrument (200). The manner in which the use data is read by reader (210) depends on the type of data storage component (222). With some types, such a EPROM and EEPROM communication may occur over direct contact electrical connections, which may be momentarily if long enough for the communication. With other types, such as an RFID chip, communication may occur by radio frequency. An example of an RFID chip is the Hitachi Mu RFID chip.

Figure 5:
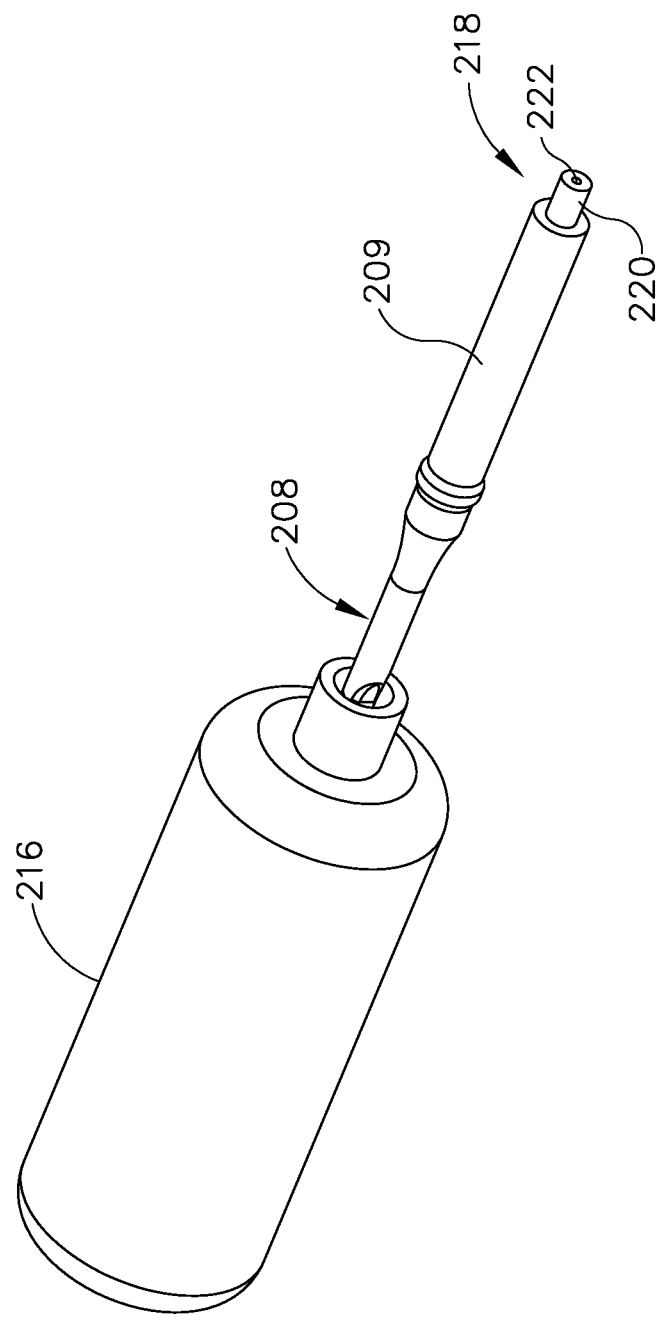
FIG. 5 depicts a perspective view of the distal portion of the waveguide and blade of FIG. 3 and an exemplary blade cartridge.

Data storage component (222) is associated with distal acoustic portion (208). In FIG. 5, data storage component (222) is disposed at the proximal end of proximal portion (218), and may be attached using any suitable means, such as adhesive. Data storage component (222) may be disposed at any suitable location on distal acoustic portion (208) or on any suitable item associated with distal acoustic portion (208), such as packaging therefor or cartridge (216). Data storage component (222) contains use data. Use data comprises data related to limits placed on the use of the distal acoustic portion (208), such as number of uses, total time used, etc. Use data includes data which may be written to data storage component (222) during use or as a result of use. Use data also includes information identifying the end effector, including for example model number, serial number and manufacturer. In some variations, data storage component (222) is a read-only component that simply provides a unique identifier for distal acoustic portion (208). In some such variations, some other component of the system (e.g., reader (210), use control module (224), generator (116), etc.) stores usage data associated with distal acoustic portion (208), based on the unique identifier assigned to distal acoustic portion (208).

Data storage component (222) may be of any suitable type for storing a unique identifier and/or use data that maintains the data at least through the useful life of distal acoustic portion (208), such as non-volatile electronic memory. In some versions the data may be overwritten, supplemented, rendered non-readable or destroyed as a result of being read/written, as a result of coupling with proximal portion of waveguide (228), as a result of use, or as a result of post use treatment of distal acoustic portion (208) such as cleaning. Data storage component (222) may also be adapted to be writable, in which case a writer may be included, such as combined with reader (210), adapted to write data in addition to reading data. Examples of types of data storage component (222) include EPROM, EEPROM, RFID. Other suitable examples will be apparent to those of ordinary skill in the art in view of the teachings herein.

Identifying data and/or use data read by reader (210) is communicated to use control module (224). While use control module (224) is shown in FIG. 4 as being separate from body (202), it should be understood that use control module (224) may be located within body (202). As another merely illustrative example, use control module (224) may be incorporated into generator (116). In some such versions, the hardware of a conventional generator (116) may be configured using software and/or firmware to provide the operability of use control module (224) as described below. The manner in which the use data is read by reader (210) depends on the type of data storage component (222). With some types, such a EPROM and EEPROM, communication may occur over direct contact electrical connections, which may be momentarily if long enough for the communication. With other types, such as an RFID chip, communication may occur by radio frequency. An example of an RFID chip is the Hitachi Mu RFID chip.

Communication between reader (210) and use control module (224) may be by any suitable means, including any suitable wired or wireless forms of communication.

Use control module (224) is adapted determine whether the use data meets one or more usage parameters, and to enable operation of distal acoustic portion (208) if the use data is determined to meet one or more usage parameters. A usage parameter comprises a condition under which distal acoustic portion (208) may be operated. For example, a usage parameter may require authentication of distal acoustic portion (208) such as that distal acoustic portion (208) is compatible with the specific surgical instrument. A usage parameter may require that the prior usage of distal acoustic portion (208) does not exceed a usage limit. Usage parameters may be stored in any suitable and accessible location, including being stored on data storage component (222).

Usage parameters may be expressed/defined by any suitable criteria. Use of a distal acoustic portion (208) during a single surgical procedure may be considered to constitute one use, although what constitutes one use may be determined based on any suitable criteria. When a use is considered to have begun and ended may also be determined on any suitable criteria. Usage may be time based, such as if the amount of time that distal acoustic portion (208) is actually operated is monitored. Use control module (224) may be adapted to monitor the amount of time that distal acoustic portion (208) is actually operated.

Regardless of the criteria used for usage parameters, permitting multiple use times or time based uses requires tracking or monitoring of the use data. An example of a way to do this, and maintain control over the use of distal acoustic portion (208), is for data storage component (222) to be writable. For a usage parameter based on the number of uses, each time data storage component (222) is read, the number of uses can be increased by one, or the number of remaining uses can be decreased by one. In a variation of this example, data storage component (222) may include a plurality of write once memory locations, with each use resulting in one of the write once memory locations being used until all have been written to. Another example is configuring data storage component (222) as a Write Once Read Many, such as a WORM RFID: A unique code may be written to data storage component (222) that indicates how many times distal acoustic portion (208) may be used. Use of the particular distal acoustic portion (208) would be limited to the system that wrote the code, which could track the number of times that it read that unique code as a prerequisite to each use. It should also be understood that use data may be written to a storage feature of use control module (224), in addition to or in lieu of being written to data storage component (222).

Use control module (224) may be of any suitable configuration, such as comprising a single module which performs all of the functions of use control module (224) or comprising a plurality of modules each of which may perform a portion of the functions of use control module (224) and which may be part of discrete components. For example, reader (210) may be adapted to determine whether the use data read by reader (210) meets one or more usage parameters, and then communicate that determination directly or indirectly to the control circuitry which is adapted to enable operation of the end effector if it has been determined that the use data meets one or more usage parameters.

If data storage component (222) is not writable, then information about whether and how much the associated distal acoustic portion (208) has been used is not available in data storage component (222) to limit use thereof. In such a case, the readable presence of use data on data storage component (222) would permit distal acoustic portion (208) to be reused. Although, as discussed above, use control module (224) may be adapted to capture a unique identifier stored on the particular data storage component (222) and to not enable operation when a previously read identifier is read, in some cases nothing would prevent that distal acoustic portion (208) from being reused on an unlimited number of other systems.

Figure 6:
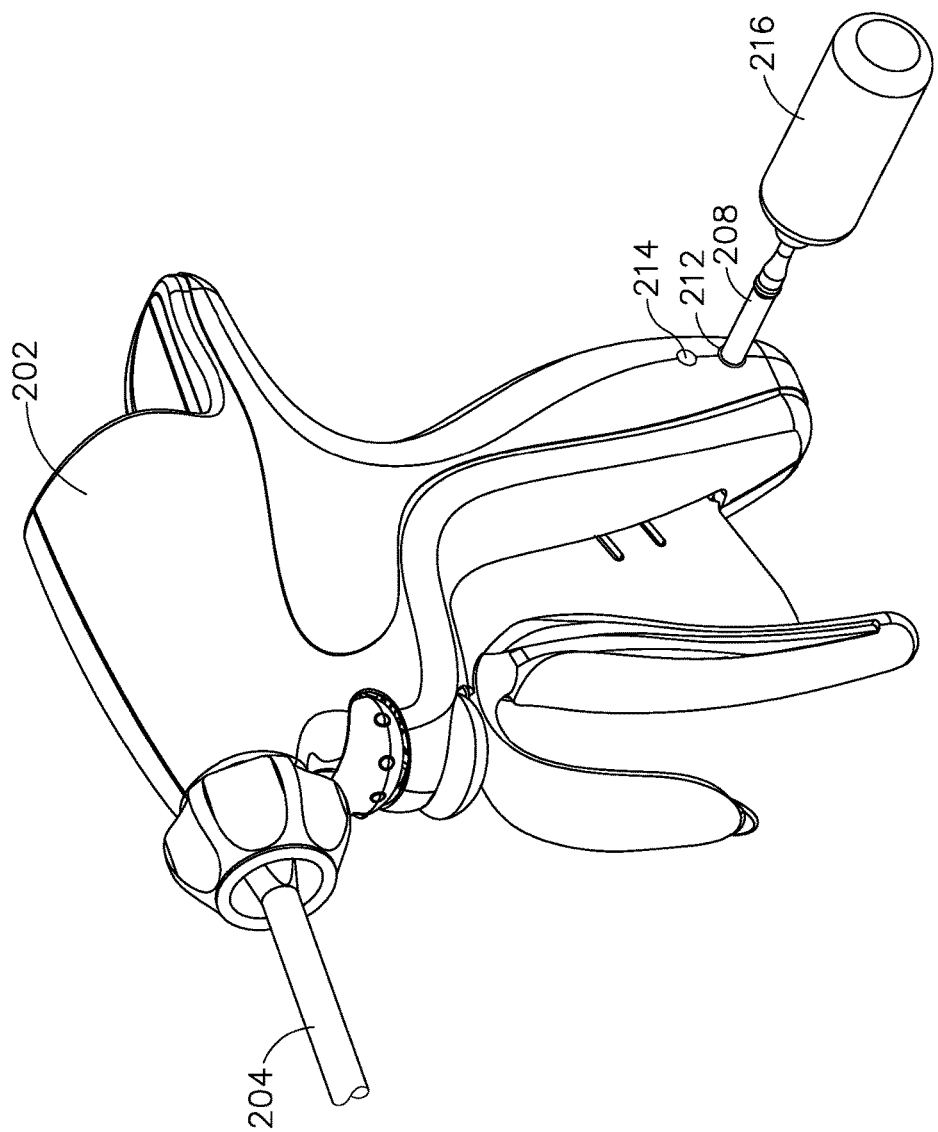
FIG. 6 depicts a perspective view of a free end of the distal portion of the waveguide and blade of FIG. 3 being inserted into an aperture of the handle assembly of the instrument of FIG. 3.

To prevent such multiple use, surgical instrument (200) may adapted to render data stored on data storage component (222) unreadable if distal acoustic portion (208) has been used. As illustrated in FIG. 6, data storage component (222), disposed at the proximal end of proximal portion (218), is placed in proximity with reader (210) by inserting the proximal end of distal acoustic portion (208) into aperture (212). If data storage component (222) comprises an RFID chip, for example, reader (210) receives the use data by radio frequency. Identifying data and/or use data read by reader (210) is communicated to use control module (224) and operation of distal acoustic portion (208) is enabled if the identifying data and/or use data meets usage parameters. If so, indicator (214) may be illuminated as an indication to proceed to use distal acoustic portion (208).

Figure 7A:
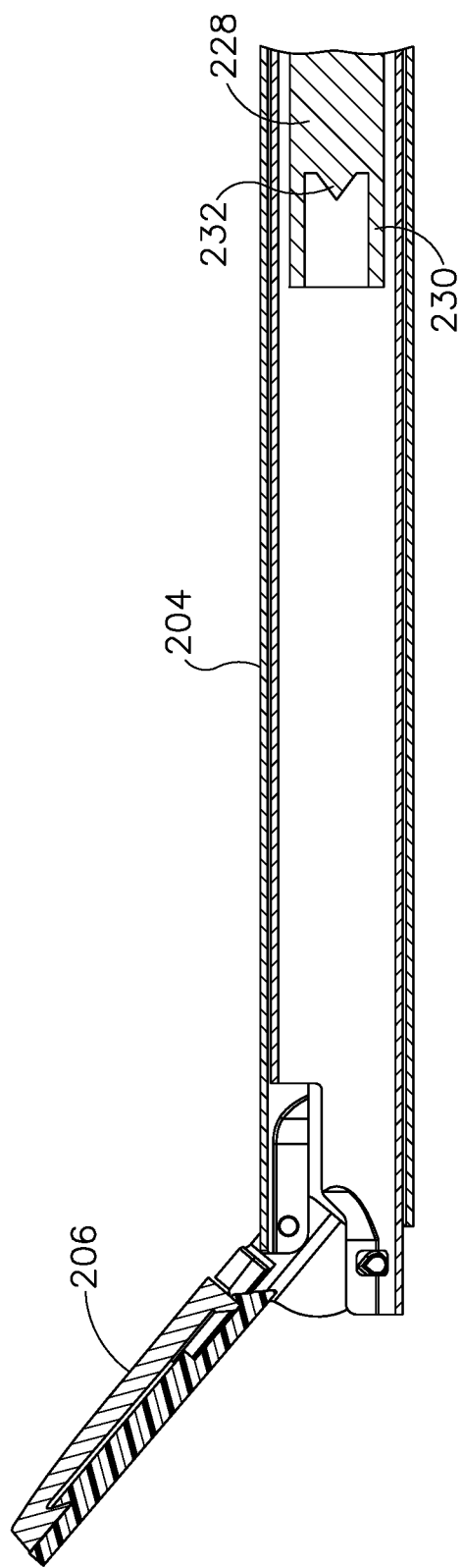
FIG. 7A depicts a side elevational view of a distal end of the shaft assembly of the instrument of FIG. 3, with the shaft assembly shown in cross-section, without the distal portion of the waveguide and blade having been assembled therewith.
Figure 7C:
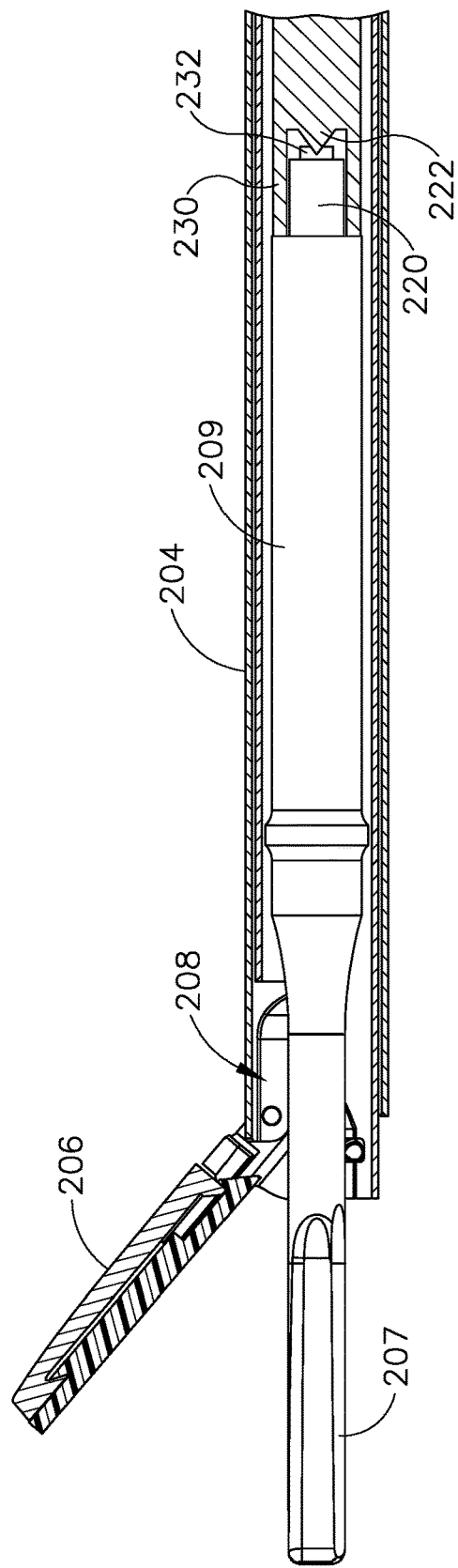
FIG. 7C depicts a side elevational view of the distal end of the shaft assembly of the instrument of FIG. 3, with the shaft assembly shown in cross-section, showing the distal portion of the waveguide and blade having been assembled therewith and the blade cartridge having been removed.

Distal acoustic portion (208) may then be withdrawn from aperture (212) and thereafter coupled to proximal portion of waveguide (228) as illustrated in FIGS. 7A-7C. Shaft assembly (204) is illustrated in cross section through its midpoint. Shaft assembly (204) is illustrated as a shaft assembly of an ultrasonic instrument, and this is depicted with proximal portion of waveguide (228) as an exemplary component to which distal acoustic portion (208) is releasably coupleable. Proximal portion of waveguide (228) includes at its distal end an attachment portion (230) that is adapted to cooperate with attachment portion (220) of distal acoustic portion (208). Attachment portion (230) includes element (232) projecting in a distal direction. Element (232) is configured with a peak, such that element (232) is in the form of a spike in the present example. It should be understood that this configuration is merely an illustrative example. Other suitable forms that element (232) may take will be apparent to those of ordinary skill in the art in view of the teachings herein.

FIG. 7B illustrates the coupling of distal acoustic portion (208) to proximal portion of waveguide (228) of shaft assembly (204) by rotating cartridge (216), such as would be required if attachment portions (220, 232) are threaded. To ensure that distal acoustic portion (208) is fully seated onto proximal portion of waveguide (228) and not over torqued, cartridge (216) may be configured with a force limiting structure, such as a torque limiter, adapted to limit the amount of force cartridge (216) can exert on distal acoustic portion (208). Various suitable forms that such a torque limited may take will be apparent to those of ordinary skill in the art in view of the teachings herein.

As can be seen in FIG. 7B and the detailed view of FIG. 8, when distal acoustic portion (208) is fully seated, the peak of element (232) projects into data storage component (222). The dimensional stack up of these features is such that element (232) makes contact with data storage component (222), permanently deforming data storage component (222) such that data stored thereon has been rendered unreadable. After distal acoustic portion (208) has been fully seated, cartridge (216) is removed. The resulting configuration is shown in FIG. 7C.

Alternatively, body (202) could be adapted to render data storage component (222) unreadable upon withdrawal of the proximal end of distal acoustic portion (208) from aperture (212) subsequent to reader (210) reading the data on data storage component (222). This diminishes the benefit from inserting a readable data storage component (222) into aperture (212) to be read (and its data rendered unreadable) and thereafter coupling to that surgical instrument a different previously used distal acoustic portion (208). As yet another merely illustrative alternative, if data storage component (222) is carried by cartridge (216), data storage component (222) may be rendered unreadable upon the removal of distal acoustic portion (208) from cartridge (216) upon coupling distal acoustic portion (208) with proximal portion of waveguide (228). Various suitable ways in which cartridge (216) and distal acoustic portion (208) may be configured to render a storage component of distal acoustic portion (208) unreadable upon removal of distal acoustic portion (208) from cartridge (216) will be apparent to those of ordinary skill in the art in view of the teachings herein.

B. Exemplary Surgical Instrument with Optical Code

Figure 9:
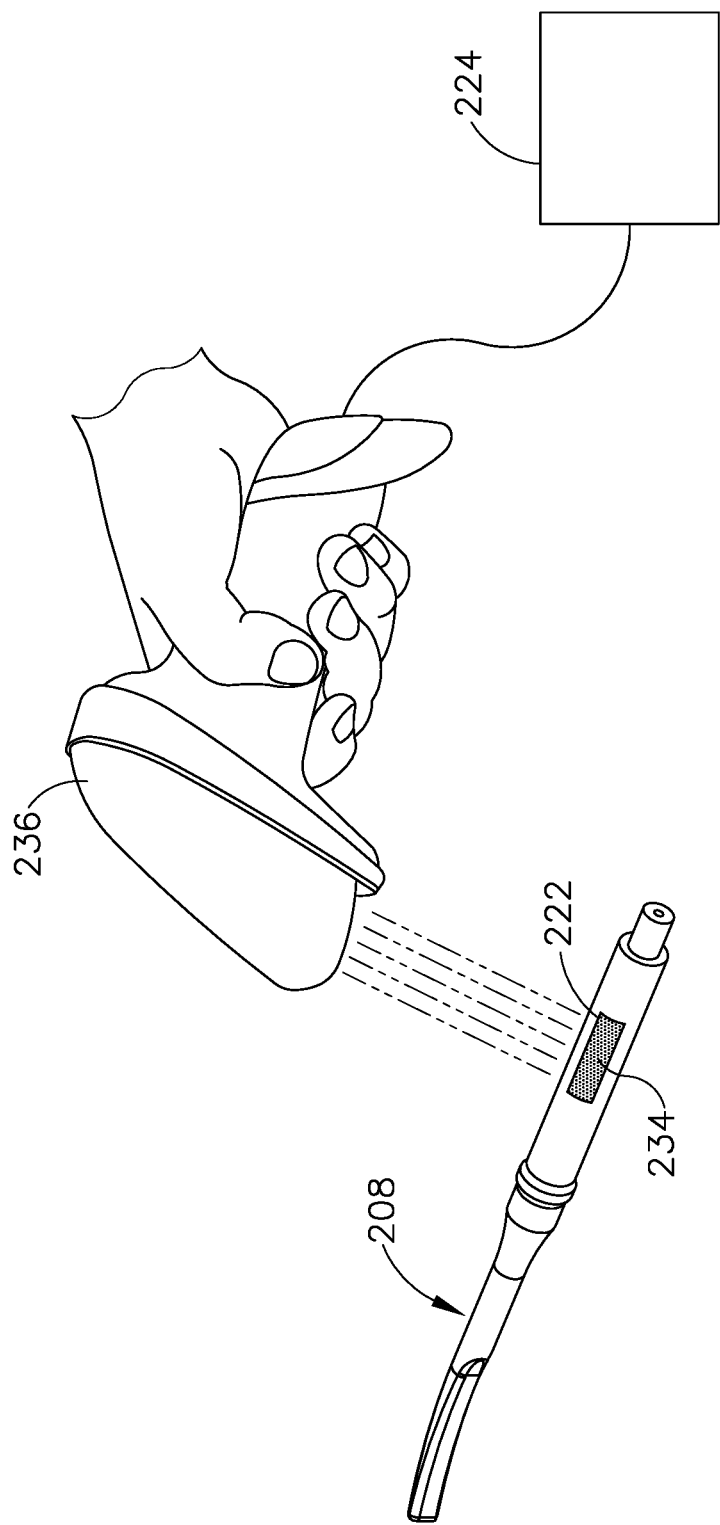
FIG. 9 depicts a perspective view of an exemplary alternative distal portion of an ultrasonic waveguide and blade that is suitable for incorporation into the instrument of FIG. 3.

As mentioned above, data storage component (222) may be of any suitable type for storing identifying data and/or use data that maintains the data at least through the useful life of distal acoustic portion (208). FIG. 9 illustrates a variation of data storage component (222) associated with distal acoustic portion (208) that stores data as indicia (234). Indicia (234) may be deposed on distal acoustic portion (208) by any suitable manner, such as laser etching or printing. Indicia (234) may be of any form suitable to contain the use data, and is illustrated in FIG. 9 as dotcode. Alternatively, any other suitable form of optical code may be used, including but not limited to a barcode or QR code, etc. Dotcode reader (236) is adapted to read the data of data storage component (222). If no dotcode is scanned, or if a scanned dotcode matches a previously read dotcode, use control module (224) will not enable operation of distal acoustic portion (208).

The dotcode of data storage component (222) may be adapted to become unreadable when distal acoustic portion (208) is cleaned, one or more times, to prevent reuse of distal acoustic portion (208) beyond a permitted number of uses. Various suitable ways in which dotcode may be rendered unreadable after distal acoustic portion (208) undergoes one or more cleaning processes will be apparent to those of ordinary skill in the art in view of the teachings herein.

IV. Exemplary Method of Tracking Instrument Component Usage

Figure 10:
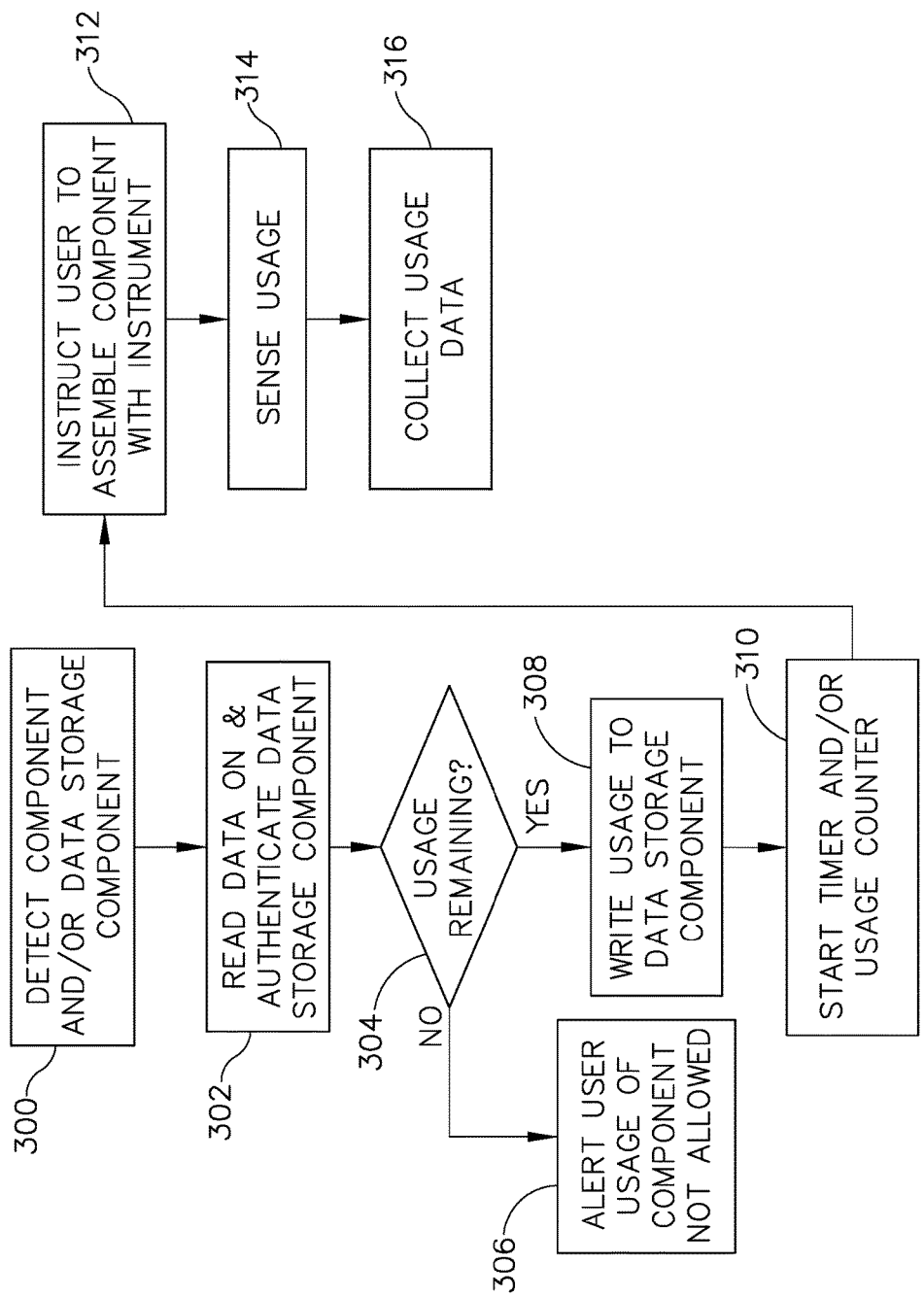
FIG. 10 depicts a flowchart showing steps of an exemplary method of determining usage of a medical device component.

FIG. 10 shoes a flow chart of steps of an exemplary method of determining usage of a medical device component, such as distal acoustic portion (208). At step (300), the medical device component or a data storage component is detected. Next, at step (302), data stored on the data storage component is read. At step (302), the data storage component may be authenticated.

At the next step, step (304), it is determined whether there is usage remaining for the medical device component. If there is not, the user will be alerted at step (306) that the use of the medical device component is not allowed, and no further steps will be taken.

If at step (304) it is determined that there is usage remaining for the medical device component, at step (308), usage data for the device will be written to the data storage component. Alternatively, usage data for the device may be written to some other component (e.g., use control module (224)). At step (310), a timer will be started to track the length of time the medical device component is used; and/or a usage counter will be started to track the number of times the medical device component is used.

Following step (310), the user is instructed at step (312) to assemble, or couple, the medical device component with the rest of the instrument. During use of the medical device component, usage thereof is sensed at step (314). At step (316), usage data relevant to the end effector is collected.

V. Exemplary Combinations

The following examples relate to various non-exhaustive ways in which the teachings herein may be combined or applied. It should be understood that the following examples are not intended to restrict the coverage of any claims that may be presented at any time in this application or in subsequent filings of this application. No disclaimer is intended. The following examples are being provided for nothing more than merely illustrative purposes. It is contemplated that the various teachings herein may be arranged and applied in numerous other ways. It is also contemplated that some variations may omit certain features referred to in the below examples. Therefore, none of the aspects or features referred to below should be deemed critical unless otherwise explicitly indicated as such at a later date by the inventors or by a successor in interest to the inventors. If any claims are presented in this application or in subsequent filings related to this application that include additional features beyond those referred to below, those additional features shall not be presumed to have been added for any reason relating to patentability.

Example 1

An apparatus comprising: (a) a body; (b) a shaft assembly extending distally from the body, wherein the shaft assembly includes a support portion; (c) an end effector portion, wherein the end effector portion is configured to selectively couple with the support portion of the shaft assembly; (d) a data storage component associated with the end effector portion, the data storage component containing data uniquely associated with the end effector portion; (e) a reader adapted to read the data from the data storage component; and (f) a use control adapted to enable operation of the end effector portion if the data meets at least one usage parameter.

Example 2

The apparatus of Example 1, wherein the data storage component is carried by the end effector portion.

Example 3

The apparatus of any one or more of Examples 1 through 2, wherein the data storage component comprises a non-volatile electronic memory.

Example 4

The apparatus of any one or more of Examples 1 through 3, wherein the support portion is adapted to render the data stored on the data storage component unreadable as a result of the end effector portion being coupled to the support portion.

Example 5

The apparatus of Example 4, wherein the support portion is adapted to physically deform the data storage component.

Example 6

The apparatus of Example 5, wherein the support portion comprises a spike, wherein the spike is configured to physically deform the data storage component.

Example 7

The apparatus of any one or more of Examples 1 through 6, wherein the support portion comprises an acoustic waveguide, wherein the end effector portion comprises an acoustic assembly configured to receive ultrasonic vibrations from the acoustic waveguide.

Example 8

The apparatus of any one or more of Examples 1 through 7, wherein the data reader is carried by the body.

Example 9

The apparatus of any one or more of Examples 1 through 8, wherein the at least one usage parameter comprises a maximum number of times the end effector portion may be used.

Example 10

The apparatus of Example 9, wherein the maximum number of times the end effector portion may be used is one.

Example 11

The apparatus of any one or more of Examples 1 through 10, wherein the data storage component comprises indicia.

Example 12

The apparatus of any one or more of Examples 1 through 11, wherein the data is stored by the data storage component as an optical code.

Example 13

The apparatus of any one or more of Examples 1 through 12, wherein the data comprises data indicative of remaining permitted uses of the end effector portion.

Example 14

The apparatus of any one or more of Examples 1 through 13, further comprising a cartridge, wherein the cartridge is configured to carry the end effector portion prior to and during coupling of the end effector portion with the support portion.

Example 15

The apparatus of Example 14, wherein the data storage component is carried by the cartridge.

Example 16

The apparatus of any one or more of Examples 14 through 15, wherein the cartridge is adapted to limit how much force can be exerted by the cartridge on the end effector portion while the cartridge is being used to couple the end effector portion to the support portion.

Example 17

The apparatus of any one or more of Examples 1 through 16, wherein the end effector portion comprises an ultrasonic blade.

Example 18

The apparatus of Example 17, wherein the end effector portion further comprises a distal waveguide portion.

Example 19

An apparatus comprising: (a) an ultrasonic end effector portion, wherein the ultrasonic end effector portion comprises: (i) an ultrasonic blade, and (ii) a distal waveguide portion; (b) a data storage component associated with the ultrasonic end effector portion, the data storage component containing data uniquely associated with the ultrasonic end effector portion; (c) a shaft assembly comprising a proximal waveguide portion, wherein the distal waveguide portion is configured to couple with the proximal waveguide portion; (d) a reader adapted to read the data of the data storage component; and (e) a use control adapted to enable operation of the ultrasonic blade if the data of the data storage component meets at least one usage parameter.

Example 20

An apparatus comprising: (a) an ultrasonic end effector portion, wherein the ultrasonic end effector portion comprises: (i) an ultrasonic blade, and (ii) a distal waveguide portion, wherein the distal waveguide portion has a proximal end, the proximal end comprising a first attachment portion; (b) a non-volatile electronic memory data storage component carried by the first attachment portion, the non-volatile electronic memory containing data uniquely associated with the ultrasonic end effector portion; and (c) a shaft assembly comprising a proximal waveguide portion, the proximal waveguide portion comprising a distal end, the distal end comprising a second attachment portion, wherein the first attachment portion is configured to couple with the second attachment portion, wherein the second attachment portion adapted to physically deform the non-volatile electronic memory such that the data cannot be read after the first attachment portion is coupled with the second attachment portion.

VI. Miscellaneous

It should be understood that any of the versions of instruments described herein may include various other features in addition to or in lieu of those described above. By way of example only, any of the instruments described herein may also include one or more of the various features disclosed in any of the various references that are incorporated by reference herein. It should also be understood that the teachings herein may be readily applied to any of the instruments described in any of the other references cited herein, such that the teachings herein may be readily combined with the teachings of any of the references cited herein in numerous ways. Other types of instruments into which the teachings herein may be incorporated will be apparent to those of ordinary skill in the art.

It should also be understood that any ranges of values referred to herein should be read to include the upper and lower boundaries of such ranges. For instance, a range expressed as ranging "between approximately 1.0 inches and approximately 1.5 inches" should be read to include approximately 1.0 inches and approximately 1.5 inches, in addition to including the values between those upper and lower boundaries.

It should be appreciated that any patent, publication, or other disclosure material, in whole or in part, that is said to be incorporated by reference herein is incorporated herein only to the extent that the incorporated material does not conflict with existing definitions, statements, or other disclosure material set forth in this disclosure. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

Versions of the devices described above may have application in conventional medical treatments and procedures conducted by a medical professional, as well as application in robotic-assisted medical treatments and procedures. By way of example only, various teachings herein may be readily incorporated into a robotic surgical system such as the DAVINCI™ system by Intuitive Surgical, Inc., of Sunnyvale, Calif. Similarly, those of ordinary skill in the art will recognize that various teachings herein may be readily combined with various teachings of U.S. Pat. No. 6,783,524, entitled "Robotic Surgical Tool with Ultrasound Cauterizing and Cutting Instrument," published Aug. 31, 2004, the disclosure of which is incorporated by reference herein.

Versions described above may be designed to be disposed of after a single use, or they can be designed to be used multiple times. Versions may, in either or both cases, be reconditioned for reuse after at least one use. Reconditioning may include any combination of the steps of disassembly of the device, followed by cleaning or replacement of particular pieces, and subsequent reassembly. In particular, some versions of the device may be disassembled, and any number of the particular pieces or parts of the device may be selectively replaced or removed in any combination. Upon cleaning and/or replacement of particular parts, some versions of the device may be reassembled for subsequent use either at a reconditioning facility, or by an operator immediately prior to a procedure. Those skilled in the art will appreciate that reconditioning of a device may utilize a variety of techniques for disassembly, cleaning/replacement, and reassembly. Use of such techniques, and the resulting reconditioned device, are all within the scope of the present application.

By way of example only, versions described herein may be sterilized before and/or after a procedure. In one sterilization technique, the device is placed in a closed and sealed container, such as a plastic or TYVEK bag. The container and device may then be placed in a field of radiation that can penetrate the container, such as gamma radiation, x-rays, or high-energy electrons. The radiation may kill bacteria on the device and in the container. The sterilized device may then be stored in the sterile container for later use. A device may also be sterilized using any other technique known in the art, including but not limited to beta or gamma radiation, ethylene oxide, or steam.

Having shown and described various embodiments of the present invention, further adaptations of the methods and systems described herein may be accomplished by appropriate modifications by one of ordinary skill in the art without departing from the scope of the present invention. Several of such potential modifications have been mentioned, and others will be apparent to those skilled in the art. For instance, the examples, embodiments, geometrics, materials, dimensions, ratios, steps, and the like discussed above are illustrative and are not required. Accordingly, the scope of the present invention should be considered in terms of the following claims and is understood not to be limited to the details of structure and operation shown and described in the specification and drawings.

We claim:

1. An apparatus comprising:
   (a) a body;
   (b) a shaft assembly extending distally from the body, wherein the shaft assembly includes a support portion;
   (c) an end effector portion, wherein the end effector portion is configured to selectively couple with the support portion of the shaft assembly;
   (d) a data storage component associated with the end effector portion, the data storage component comprising a set of use data associated with the end effector portion, wherein the data storage component comprises a non-volatile electronic memory;
   (e) a non-volatile electronic memory reader operable to receive the set of use data from the data storage component when positioned to allow a proximity connection to the non-volatile electronic memory; and
   (f) a use control module comprising a processor and positioned within the body, wherein the processor is configured to:
      (i) receive the set of use data from the non-volatile electronic memory reader,
      (ii) determine that the end effector portion is usable based upon the set of use data and a set of usage parameters, and
      (iii) where the end effector portion is usable, enable the end effector portion,
   wherein the support portion is adapted to render the data stored on the data storage component unreadable as a result of the end effector portion being coupled to the support portion.

2. The apparatus of claim 1, wherein:
   (a) the data storage component is carried by a proximal end of the end effector portion,
   (b) the non-volatile electronic memory reader is positioned in the body and comprises an aperture configured to receive the proximal end, and
   (c) the non-volatile electronic memory reader is configured to receive the data from the data storage component when the proximal end is positioned within the aperture.

3. The apparatus of claim 1, wherein the support portion is adapted to physically deform the data storage component.

4. The apparatus of claim 3, wherein the support portion comprises a spike, wherein the spike is configured to physically deform the data storage component.

5. The apparatus of claim 1, wherein:
   (a) the support portion comprises an acoustic waveguide, wherein the end effector portion comprises an acoustic assembly configured to receive ultrasonic vibrations from the acoustic waveguide;
   (b) the non-volatile electronic memory comprises an RFID chip, and
   (c) the non-volatile electronic memory reader is configured to receive the set of use data when the proximity connection to the non-volatile electronic memory is a wireless RFID connection between the non-volatile electronic memory reader and the non-volatile electronic memory.

6. The apparatus of claim 1, wherein:
   (a) the non-volatile electronic memory reader is carried by the body;
   (b) the non-volatile electronic memory comprises an EEPROM chip, and
   (c) the non-volatile electronic memory reader is configured to receive the set of use data when the proximity connection to the non-volatile electronic memory is an electrical connection between the non-volatile electronic memory reader and the EEPROM chip.

7. The apparatus of claim 1, wherein the data comprises data indicative of remaining permitted uses of the end effector portion.

8. The apparatus of claim 1, further comprising a cartridge, wherein the cartridge is configured to carry the end effector portion prior to and during coupling of the end effector portion with the support portion.

9. The apparatus of claim 8, wherein the cartridge is configured to carry the data storage component before and after coupling of the end effector portion with the support portion.

10. The apparatus of claim 8, wherein the cartridge is adapted to limit how much force can be exerted by the cartridge on the end effector portion while the cartridge is being used to couple the end effector portion to the support portion.

11. The apparatus of claim 1, wherein the end effector portion comprises an ultrasonic blade.

12. The apparatus of claim 11, wherein the end effector portion further comprises a distal waveguide portion.

13. An apparatus comprising:
   (a) an ultrasonic end effector portion, wherein the ultrasonic end effector portion comprises:
      (i) an ultrasonic blade, and
      (ii) a distal waveguide portion, wherein the distal waveguide portion has a proximal end, the proximal end comprising a first attachment portion;
   (b) a non-volatile electronic memory data storage component carried by the first attachment portion, the non-volatile electronic memory data storage component containing data uniquely associated with the ultrasonic end effector portion; and
   (c) a shaft assembly comprising a proximal waveguide portion, the proximal waveguide portion comprising a distal end, the distal end comprising a second attachment portion, wherein the first attachment portion is configured to couple with the second attachment portion, wherein the second attachment portion is adapted to physically deform the non-volatile electronic memory data storage component such that the data cannot be read after the first attachment portion is coupled with the second attachment portion.

14. An apparatus comprising:
(a) a body;
(b) a shaft assembly extending distally from the body, wherein the shaft assembly includes a support portion;
(c) an end effector portion, wherein the end effector portion is configured to selectively couple with the support portion of the shaft assembly;
(d) a data storage component associated with the end effector portion, the data storage component comprising a set of use data associated with the end effector portion, wherein the data storage component comprises a non-volatile electronic memory;
(e) a non-volatile electronic memory reader operable to receive the set of use data from the data storage component when positioned to allow a proximity connection to the non-volatile electronic memory; and
(f) a use control module comprising a processor and positioned within the body, wherein the processor is configured to:
(i) receive the set of use data from the non-volatile electronic memory reader,
(ii) determine that the end effector portion is usable based upon the set of use data and a set of usage parameters, and
(iii) where the end effector portion is usable, enable the end effector portion,
wherein the non-volatile electronic memory reader is configured to modify the state of the non-volatile electronic memory to render the set of use data unreadable by the non-volatile electronic memory reader after receiving the set of use data.

15. The apparatus of claim 14, wherein the processor is configured to:
(i) when the end effector portion is determined to be usable, provide an indication to a user via a visual indicator of the non-volatile electronic memory reader that the end effector portion is usable, and
(ii) when the end effector portion is not determined to be usable, provide an indication to the user via the visual indicator that the end effector portion is unusable.

* * * * *